United States Patent [19]

Login et al.

[11] Patent Number: 4,515,721

[45] Date of Patent: May 7, 1985

[54] PROCESS FOR THE PRODUCTION OF FATTY ACID ESTERS OF HYDROXYALKYL SULFONATE SALTS

[75] Inventors: Robert B. Login, Media; Ismail L. Walele, Aston; Richard J. Otterson, Glenolden, all of Pa.

[73] Assignee: Jordan Chemical Company, Folcroft, Pa.

[21] Appl. No.: 589,170

[22] Filed: Mar. 13, 1984

Related U.S. Application Data

[63] Continuation-in-part of Ser. No. 424,281, Sep. 27, 1982, abandoned.

[51] Int. Cl.$^3$ .................. C07C 143/90; C11D 1/28
[52] U.S. Cl. .................................................. 260/400
[58] Field of Search ........................................ 260/400

[56] References Cited

U.S. PATENT DOCUMENTS

| Re. 23,823 | 5/1954 | Molteni et al. ............. | 260/400 |
|---|---|---|---|
| 1,881,172 | 10/1932 | Daimler et al. . | |
| 2,303,582 | 12/1942 | Russell et al. ............. | 260/400 |
| 2,307,953 | 1/1943 | Potter . | |
| 2,316,719 | 4/1943 | Russell ...................... | 260/400 |
| 2,328,931 | 9/1943 | Steik ......................... | 260/400 |
| 2,857,370 | 10/1958 | Sundberg . | |
| 2,863,887 | 12/1958 | Becher ....................... | 260/400 |
| 2,898,352 | 8/1959 | Schenck ..................... | 260/400 |
| 2,923,724 | 2/1960 | Anderson et al. .......... | 260/400 |
| 3,029,264 | 4/1962 | Alphen ....................... | 260/400 |
| 3,151,136 | 9/1964 | Koczozowski et al. ..... | 260/400 |
| 3,167,570 | 1/1965 | Bohunek ..................... | 260/400 |
| 3,320,292 | 5/1967 | Cahn et al. ................. | 260/400 |
| 3,383,396 | 5/1968 | Cahn et al. ................. | 260/400 |
| 3,394,155 | 7/1968 | Cahn et al. ................. | 260/400 |
| 3,420,857 | 1/1969 | Holland et al. ............ | 260/400 |
| 3,420,858 | 1/1969 | McCrimlisk ................ | 260/400 |
| 3,429,136 | 2/1969 | Holt et al. . | |
| 3,745,181 | 7/1973 | Wrigley et al. ............ | 260/400 |
| 3,880,897 | 4/1975 | Landy ........................ | 260/400 |
| 3,997,576 | 12/1976 | Oghoshi et al. ............ | 260/400 |

FOREIGN PATENT DOCUMENTS 1121045  1/1962  Fed. Rep. of Germany .

*Primary Examiner*—Helen M. S. Sneed
*Attorney, Agent, or Firm*—Dann, Dorfman, Herrell and Skillman

[57] ABSTRACT

Fatty acid esters of hydroxyalkyl sulfonates are prepared by heating an excess of the fatty acids with the sulfonate until the water of condensation is removed. The hot crude ester is then quenched by immersion in an excess of cooled liquid, in which the ester product is soluble but in which unreacted, excess fatty acids are insoluble. The resulting slurry is filtered to separate the relatively pure ester from the quenching liquid containing dissolved free fatty acid. Isopropanol is the preferred quenching liquid.

17 Claims, No Drawings

PROCESS FOR THE PRODUCTION OF FATTY ACID ESTERS OF HYDROXYALKYL SULFONATE SALTS

BACKGROUND OF THE INVENTION

This application is a continuation-in-part of Ser. No. 424,281, filed Sept. 27, 1982 now abandoned.

This invention relates to the preparation of surface-active materials and more particularly to the preparation of esters of fatty acids with hydroxyalkyl sulfonates, also known as isethionates, said esters having the general formula RCOOR′SO$_3$M. In this formula R represents the aliphatic hydrocarbon residue of a fatty acid containing from 6 to 24 carbon atoms, R′ represents a divalent hydrocarbon radical containing from 2 to 4 carbon atoms, and M represents an alkali metal. These compounds are well known as valuable detergents and wetting agents.

The preparation of such esters by the direct esterification of the fatty acid with the hydroxyalkyl sulfonate has presented difficulties because of the high temperature required to obtain a suitable conversion. A more rapid reaction takes place with the fatty acid chloride, but this is more expensive and may lead to corrosion problems. The early patent to Daimler, U.S. Pat. No. 1,881,172 employed this process.

At the temperatures required for the direct esterification reaction, usually in the range of 220° to 250° C., the molten reaction product rapidly degrades in color and loses activity. Various expedients are taught in the art to accelerate the reaction or to avoid color degradation or to purify the crude product obtained by direct esterification.

REACTION ACCELERATORS

Sundberg in U.S. Pat. No. 2,857,370 teaches the use of a boron-containing compound as a catalyst at reduced pressure or in an inert atmosphere. Anderson et al. in U.S. Pat. No. 2,923,724 disclose the use of a phosphorus containing compound such as a phosphoric acid or phosphate as an accelerator. In U.S. Pat. No. 3,151,136 (Koczorowski et al.) it is taught that quantitative yields may be obtained at relatively low temperatures by using hydroxyalkyl sulfonic acid which is substantially free from its salts, while operating at reduced pressure. The reaction product in this case must be neutralized to obtain the desired metal salt, introducing a further step. Zinc and zirconium salts are disclosed as catalysts for the esterification reaction by Cahn in U.S. Pat. No. 3,320,292 and U.S. Pat. No. 3,383,396, respectively.

A number of prior art patents teach the use of modifications of the fatty acid to improve the reactivity. Thus, Schenck in U.S. Pat. No. 2,898,352 teaches the use of a mixed borate-fatty acid anhydride. This patent further teaches that the resulting borax may be removed from the reaction product by filtration of the molten product or by solvent extraction, using either organic solvents such as hydrocarbons, alcohols or esters to remove the fatty acid isethionic acid esters or aqueous extractions to remove the borax and sodium isethionate. Wrigley et al. in U.S. Pat. No. 3,745,181 describes the use of isopropanol fatty esters to react with hydroxyalkyl sulfonate salts.

AVOIDING COLOR DEGRADATION

Several of the patents already mentioned teach the desirability of maintaining a nitrogen atmosphere in order to avoid oxidation of the reaction product and also the use of reduced pressure to permit the removal of the water formed during the condensation reaction at a lower temperature. Holt et al. in U.S. Pat. No. 3,429,136 teaches that degradation of the hot reaction product may be avoided by injecting cold water directly into the molten crude condensate to cool the mass below a temperature at which rapid discoloration would occur and that this can be done without causing appreciable hydrolysis of the ester.

PURIFICATION

The crude reaction product ordinarily contains unreacted fatty acid, sulfonate or both. McCrimlisk in U.S. Pat. No. 3,420,858 teaches the removal of lower fatty acids by a two-stage vacuum stripping, in which higher fatty acids are added to the reaction mixture after some of the lower acids have been removed, in order to maintain fluidity and to make possible the further removal of the lower fatty acids. Molteni in U.S. Pat. No. Re. 23,823 uses an excess of sodium isethionate in his reaction and removes the excess after the esterification has taken place by dispersing the product in water, evaporating and precipitating out the desired fatty acid ester. Russell et al. U.S. Pat. No. 2,303,582, Potter U.S. Pat. No. 2,307,953, and Russell U.S. Pat. No. 2,316,719 all describe methods for separating inorganic salts from organic sulfonates or sulfates by forming two-phase liquid systems in which the inorganic salt is in aqueous solution and the organic compound is dissolved in an organic solvent, which may be an alcohol such as isopropanol. The aqueous layer is drawn off to remove the inorganic salt. Landy in U.S. Pat. No. 3,880,897 describes a process in which a hydroxyalkyl sulfonate is reacted with a fatty acid halide in anhydrous dialkyl ketone. When the reaction is complete, the mixture is cooled and the insoluble ester is filtered from the dialkyl ketone solvent, washed and dried.

SUMMARY OF INVENTION

It has now been found possible to prepare surfactants of the class described above by a process which involves the direct esterification of the fatty acid with the hydroxyalkyl sulfonate to yield a product having excellent color and activity and low fatty acid content. The process makes efficient use of the raw materials employed and employs easily performed operations to give a product of desirable physical form.

According to the present invention, fatty acid esters of hydroxyalkyl sulfonates having the formula RCOOR′SO$_3$M, where R represents the aliphatic hydrocarbon residue of a fatty acid containing from 6 to 24 carbon atoms, R′ represents a divalent hydrocarbon radical containing from 2 to 4 carbon atoms, and M represents an alkali metal, are prepared by condensing such a fatty acid or a mixture of such fatty acids with a hydroxyalkyl sulfonate of the formula HOR′SO$_3$M. In this process, a molecular excess of the fatty acid is heated together with the hydroxyalkyl sulfonate, while sparging with an inert gas to a temperature of 200° to 250° C. for a sufficient time to remove the water of condensation. The hot crude fatty acid ester is then quenched by immersion in a liquid which is at a temperature lower than the crude reaction mixture to effect rather rapid cooling of the reaction mixture. Liquids suitable for this purpose are those in which the ester is substantially insoluble and the unreacted fatty acid is soluble. Quenching of the crude reaction mixture in this fashion forms a slurry in which the solid phase comprises relatively pure ester and the liquid phase comprises the quenching liquid and unreacted fatty acid. The solid phase is thereafter separated from the liquid phase of the slurry, preferably by filtration. Preferably the filtrate is then distilled to recover free fatty acid and quench liquid.

DETAILED DESCRIPTION OF INVENTION

Suitable fatty acids for use in the process of this invention are those containing from 6 to 24 carbon atoms. They include the unsubstituted, saturated or unsaturated straight-chain fatty acids, such as those derived from coconut, palm kernel and babassu oils. Such fatty acids are available in a variety of grades. When derived from naturally occurring oils, they usually comprise a mixture of fatty acids of varying chain lengths. If higher molecular weight condensates are desired, then fatty acids derived from glycerides which contain palmitic or stearic acids may be employed, for example those derived from tallow, soybean, rape seed and sunflower oils. Either unsaturated or saturated compositions can be employed, but the latter will afford lighter colored condensates. Fatty acids derived from coconut oil, comprising a mixture of $C_8$ to $C_{18}$ fatty acids represent a preferred fatty acid reactant.

The hydroxyalkyl sulfonate used in the reaction, commonly referred to as an isethionate salt, has the general structure $HOR'SO_3M$. The divalent hydrocarbon radical R' contains 2 to 4 carbon atoms and specifically may be ethylene, methylethylene, dimethylethylene, propylene or butylene. M is an alkali metal cation, especially sodium or potassium. The preparation of isethionate salts is well known to those skilled in the art and is described for example in U.S. Pat. No. 2,810,747 and U.S. Pat. No. 2,820,818. Although the divalent alkyl radical R' can be branched, the straight-chain radicals are preferred since they tend to have greater thermal stability and will degrade in color to a lesser extent at the high temperatures necessary for the condensation reaction. Specifically preferred compounds are sodium isethionate, potassium isethionate and sodium 3-hydroxypropane sulfonate. The most important condensate commercially is based on coconut oil fatty acids and sodium isethionate.

Fatty acids present in the reaction mixture should be in molar excess in relation to the hydroxyalkyl sulfonate. Preferably the ratio of fatty acid to sulfonate should be at least about 1.1 but not higher than about 2. Excess fatty acid helps to maintain the reaction mixture in liquid form. If less than 1.1 moles of fatty acid per mole of sulfonate is used, the mixture becomes difficult to stir and almost impossible to transfer to the vessel containing the quench liquid. Excess fatty acid also tends to force the condensation reaction to go forward, thus resulting in a high utilization of the hydroxyalkyl sulfonate. Finally, excess fatty acid is readily removed during the quenching and filtration steps. No harm is done by using an even greater excess of fatty acid than corresponds with a 2 to 1 ratio, except that it then must be removed during the purification steps.

The optimum amount of excess fatty acid will vary somewhat according to the particular fatty acid and hydroxyalkyl sulfonate that is used.

It is convenient to add the hydroxyalkyl sulfonate in aqueous solution, which may be a 40–80% by weight solution. The water so added, together with the water formed during the condensation reaction, is distilled off during the heating period. During this step, the temperature is gradually raised to 200° to 250° C. and maintained in this range until the water has been removed. Free, unreacted fatty acid also distills off at the elevated temperature and the progress of the reaction may be followed by checking the free fatty acid content of the reaction mixture. When this value becomes less than 20% by weight, the reaction is essentially complete. The acid value can be further reduced by raising the inert gas sparge rate and essentially distilling over some of the excess fatty acid. Excessive removal of unreacted fatty acid will result in thickening of the product or discoloration. The former will affect the rate of flow of the finished batch into the quench liquid. Preferably heating is continued until the free fatty acid has reached a range of 15 to 17%.

In order to reduce the temperature and time required for the reaction, any suitable promoter may be employed. Such promoters are well known in the art.

It is necessary that the reaction be carried out in a substantially oxygen-free atmosphere, since oxygen will rapidly darken the product at elevated temperatures, especially if unsaturation is present. It is thus desirable to maintain an inert gas atmosphere and this is conveniently done by sparging with nitrogen throughout the course of the reaction. The sparging is also beneficial in helping to agitate the reaction mixture and to sweep out water vapor and some unreacted fatty acid.

When the reaction is complete, the molten, crude reaction mixture is transferred directly into an excess of quench liquid maintained at a temperature below that of the reaction mixture, in order to effect rapid cooling thereof and separation of the sulfonated fatty acid ester from unreacted fatty acid and other impurities. The transfer of the hot reaction mixture into the quench liquid should be carried out as quickly as possible, consistent with avoiding local overheating of the liquid. The ester is not recrystallized from the quenching liquid but simply solidifies upon cooling to form a uniform slurry.

Any liquid in which the ester product is substantially insoluble and the unreacted fatty acid is soluble may be employed as the quench liquid in this process; however, organic liquids are preferred. The term "liquid", as used in the present context, refers to substances which are freely flowing at the maximum temperature of the reaction mixture, generally 240° C. to 250° C., and remain freely flowing within a reasonably broad range therebelow, so as to provide a readily filterable material after introduction of the ester into the quench liquid. Representative of the quench liquids which may be used in the process are: lower alcohols having 3 to 6 carbon atoms, especially isopropanol; fatty alcohols, e.g. stearyl alcohol or cetyl alcohol, and fatty alcohol ethoxylates; polyethylene glycols, e.g. polyethylene glycol (M.W. 4000) polyoxyalkylene derivatives of polyethylene glycol (commercially available as Pluronic F-127 Polyol), or polyoxyalkylene derivatives of ethylene diamine (commercially available as Tetronic 1508 Polyol); fatty triglycerides, e.g. tallow or hydrogenated tallow; fatty esters, e.g. glycerol monostearate, diethylene glycol monostearate, isopropyl myristate; fatty amides, e.g. stearyl monoethanolamide, stearyl diethanolamide, coco monoethanolamide; and paraffins. Mixtures of the foregoing quench liquids may be used, if desired. As those skilled in the art will appreciate, many of these substances are commonly used in detergent compositions. Thus the presence of a certain amount thereof in the final product is acceptable, and indeed, may actually facilitate detergent formulation.

A particularly preferred quench liquid is isopropanol. Sodium cocoyl isethionate is insoluble in isopropanol, but unreacted coconut fatty acid and neutral fatty acid esters are completely soluble therein. Quenching the reaction mixture in isopropanol gives rise to an easily filtered slurry from which a relatively pure product can be readily obtained. Moreover, any residual isopropanol in the final product may be substantially completely removed by vacuum drying.

In general, the quenching liquid should be at or below room temperature when quenching begins. However, when the substance used for quenching is normally solid at room temperature, it will be necessary to heat the substance sufficiently to render it free flowing. The volume of quenching liquid used should be 2 to 5 times that of the crude reaction product, so that cooling will occur rapidly. Cooling coils or jackets may be employed to control the temperature of the quench liquid if desired, particularly if a relatively low ratio of quenching liquid is used.

The quenching liquid should be fairly vigorously agitated during immersion of the hot crude reaction mixture therein, in order to effect rapid cooling and to avoid localized overheating and ebullition of the quenching liquid, but also to ensure the formation of small particles of the solidified ester, which minimizes the amount of quenching liquid, free fatty acid and impurities which will be occluded when the product is filtered. In general, the particle size of the ester will be smaller as the agitation is increased.

After the reaction product has been added to the quenching liquid, the resulting slurry can be pumped to a filter. The filter cake is dried, pulverized and bagged. The filtrate, containing quenching liquid, unreacted fatty acids and some neutral esters may be distilled to separate and recover these components, which may then be recycled for use in subsequent operations.

Instead of filtering, any other conventional method of separating the sulfonate ester from the quenching liquid may be used, such as centrifuging.

The purity of the fatty acid ester sulfonate will depend partly on the purity of the reactants used and partly on the efficiency of the filtration step. Residual quenching liquid containing unreacted fatty acid and neutral esters if allowed to remain on the sulfonated ester will deposit the fatty acid and neutral esters on the surface of the sulfonated ester when it is dried. It is of course appropriate to wash the filter cake with additional fresh quenching liquid in order to obtain the requisite purity. It should be understood that complete separation of all of the quench liquid from the product is not necessary. Indeed, when the quench liquid is a substance normally used in detergent compositions, the presence of a certain residual amount thereof in the final product should not be objectionable, and may even be desirable. In general, the amount of quenching liquid removed should be such as to provide an end product which is free of any adverse effects that are characteristic of an excess of fatty acid, e.g. softening, poor wash resistance, mushiness, and the like. The precise amount to be removed in a particular case will vary depending on the fatty acid ester sulfonate produced and the specific quench liquid employed, and may easily be determined by trial.

The hydroxyalkyl sulfonates used in the reaction may contain some unsulfonated glycols. During the reaction, these may form fatty glycol esters (the neutral fatty esters mentioned previously) which are soluble in certain of the quenching liquid, e.g. isopropanol, and thus readily removable from the fatty acid ester sulfonate during the filtration. These glycol esters tend to be defoamers and it is quite undesirable for them to be present in any significant amount in the end product. When the quenching liquid is distilled to separate it from the unreacted fatty acids, the glycol esters tend to remain with the unreacted fatty acid. With continuous recycling of these fatty acids, there may come a point at which the level of glycol ester is such as to impair the performance qualities of the solid product. If the Ross-Miles test indicates a loss of foam height, it is then necessary to purify the quench liquid-recovered fatty acids to remove or decompose these esters. Such a purification would entail operations such as distillation, hydrolysis, decolorization and the like, the details of which are well known to those skilled in the art of fatty acid purification.

The following examples illustrate the operation of this invention, and are not intended to limit the invention.

EXAMPLE 1

A 5-liter jacketed resin flask equipped with a nitrogen sparge, thermometer, distilling head (condenser and receiver) and a mechanical agitator was charged with 1,744.5 grams (8.53 moles) of a partially hydrogenated coconut fatty acid with the following typical specifications: saponification value of 271, acid value of 266–274 mg. KOH/g., iodine value of 5 max. cg./g., unsaponifiables of 0.5% max., moisture of 0.5% max., color of less than Gardner 1 and average molecular weight of 208, and 1725.5 grams (6.35 moles) of an aqueous solution of sodium isethionate which met the following specifications:

Appearance at 25° C.: Clear, light liquid free of foreign matter
Color, APHA: 25 max.
Active, %: 54.0–55.0%
Ethylene Glycol: 1.0% max.
Sodium sulfite, ppm: 500 max.
Iron, ppm: 10 max.
pH, as is: 9.0–10.0

To this mixture was added with stirring 3.5 grams of zinc oxide powder. Sparging with nitrogen was then begun and the mixture was heated. When the temperature of the crude mixture reached 115° C., the water associated with the sodium isethionate began to distill over. By the time the mixture reached 130° C., 366 grams had been collected; by 175° C., 650 grams were collected. From this point until the condensation was complete took four hours. The temperature was slowly raised to 250° C. over this period. A total of 817 grams of water and 31 grams of fatty acid were collected.

The course of the reaction was followed by measuring the free fatty acid content of the reaction mixture. Samples were dissolved at intervals in a 1:1 mixture of water and ethylene glycol contained in tared beakers and titrated potentiometrically with 0.5N sodium hydroxide with an automatic titrimeter. When the free fatty acid dropped below 20%, the condensation was essentially complete.

When the level of free coconut fatty acid reached 16.2%, the crude molten mixture (which assayed for 75.1% active fatty ester sulfonate by two-phase titration against standardized benzethonium chloride solution using methylene blue as the indicator) was transferred without contact with air in less than half an hour into seven liters of 99% isopropanol at ambient temperature contained in a 12-liter round bottom three neck flask equipped with a mechanical stirrer, thermometer and Graham condenser. This flask was contained in a water bath which facilitated cooling if needed.

The molten liquid crude ester immediately dispersed when it struck the isopropanol and formed a mixture which was remarkably easy to filter. The isopropanol slurry never got hotter than 70° C. When the transfer was completed, the mixture was allowed to stand overnight and was filtered under vacuum through a Buchner funnel. The filter cake was dried in an air convection oven at 140° F. for several hours and pulverized to form the powdered product. Five liters of filtrate were recovered. This was distilled to afford 4.5 liters of isopropanol and 288.5 grams of coconut fatty acids.

The steam distilled coconut fatty acid fraction collected during condensation and the fraction recovered from the isopropanol were analyzed by gas chromatography and found to have the following compositions:

| %    | SD (1) | IPA (2) |
| ---- | ------ | ------- |
| C6   | 8.3    | 0.0     |
| C8   | 75.6   | 4.5     |
| C10  | 6.1    | 5.4     |
| C12  | 9.8    | 52.6    |
| C14  | 0.3    | 19.0    |
| C16  | 0.0    | 8.4     |
| C18  | 0.0    | 7.1     |
| C18- | 0.0    | 3.0     |

(1) Steam Distilled: 97.5% of the material was fatty acids.
(2) IPA recovered: 84% of the material was fatty acids and the remainder was fatty glycol esters.

Combination of the two afforded 306 grams of recovered coconut fatty acid which was reused in Example 2.

The dry fatty acid ester sulfonate product exhibited the following analysis:
Activity (MW338): 84.7%
Free fatty matter: 8.6%
pH (5% sol'n.): 6.0
APHA Color (5% in 30% IPA): 10

EXAMPLE 2

The combined recovered fatty acids from Example 1 were added along with 1468.5 grams of fresh coconut fatty acid of the same kind used in Example 1 to the reactor previously described. Employing the same charges of sodium isethionate and zinc oxide, the process was repeated. The crude reaction product was transferred as a molten liquid when the free fatty acid content dropped to 16.7% (subsequent analysis showed 72.9% actives) to a mixture of recovered isopropanol and fresh isopropanol (60:40 respectively). The subsequently filtered and dried product had the following analysis:
Activity (M.W. 338): 85.9%
Free fatty matter: 5.38%
pH (5% aqueous): 6.33%
APHA Color (5% sol'n.): 15
Moisture by Karl Fischer: 0.5%

The yield of product was similar to that of Example 1 and was approximately 57% based on the charged starting materials. In this case, 116 grams of co-distilled fatty acid and 243 grams of isopropanol-recovered fatty acid were obtained. They analyzed as follows:

| Fatty Acid | SD (1) | IPA (2) |
| ---------- | ------ | ------- |
| C6         | 2.1    | 0       |
| C8         | 37.8   | 3.6     |
| C10        | 10.7   | 5.3     |
| C12        | 40.6   | 49.3    |
| C14        | 6.9    | 20.8    |
| C16        | 1.3    | 9.5     |
| C18        | 0.5    | 8.1     |
| C18-       | 0      | 3.2     |

(1) 99.2% of the material was fatty acids.
(2) 77.6% of the material was fatty acids and the remainder was glycol esters.

EXAMPLE 3

The combined recovered fatty acids from Example 2 plus 2434.5 grams of fresh coconut fatty acids of the same kind used in Example 1 were used in this reaction, which was carried out in the same way as the two preceding Examples. The condensation was deemed to be complete when the crude mixture exhibited a free fatty acid content of 15% (subsequent analysis showed 74.4% actives). After filtration and workup, the powdered product analyzed as follows:
Activity (MW338): 84.93%
Free fatty matter: 6.12%
pH (5% aqueous): 6.25
APHA Color (5% Sol'n.): 10

The fatty acid fractions analyzed as follows:

| Fatty Acid | SD (1) | IPA (2) |
| ---------- | ------ | ------- |
| C6         | 6.0    | 0       |
| C8         | 51.9   | 2.9     |
| C10        | 13.1   | 5.0     |
| C12        | 26.1   | 50.4    |
| C14        | 2.5    | 21.1    |
| C16        | 0.3    | 9.1     |
| C18        | 0.1    | 7.8     |
| C18-       | 0      | 3.3     |

(1) 84.4 g collected, of which 98.5% was fatty acid.
(2) 246.2 g collected, of which 73.2% was fatty acid.

Foaming characteristics of the sulfonate esters obtained in Examples 1-3 were observed by the Ross Miles Foam Height test, using in each case a 0.2% solution of the ester in soft water and carrying out the tests at 50° C. The results were as follows:

|         | Foam Height | |
| ------- | ----------- | --------------- |
| Example | Initial     | After 5 Minutes |
| 1       | 153         | 148             |
| 2       | 150         | 145             |
| 3       | 150         | 146             |

EXAMPLE 4

A crude molten (240°-250° C.) condensation product produced as in Example 1 and containing 14-18% free coconut fatty acid and 74-76% active sodium cocoyl isethionate was poured into liquid polyethylene glycol of molecular weight 4000 at such a rate as to maintain the temperature of the quench liquid between 80°-120° C. The resulting opaque mixture was transferred to a filter and most of the polyethylene glycol and coconut fatty acid was removed leaving a mixture of purified sodium cocoyl isethionate and polyethylene glycol. This mixture can be cooled and flaked and is suitable as an ingredient for use in synthetic detergent soap bar manufacture.

The recovered polyethylene glycol/fatty acid mixture was added to water, in which the polyethylene glycol is soluble. Insoluble coconut fatty acid was removed by decantation and the fatty acid recovered.

Alternatively, the fatty acid may be vacuum or steam distilled away from the polyethylene glycol. Recovered fatty acid and polyethylene glycol can be recycled for use in subsequent operation of the process.

While certain preferred embodiments of the present invention have been described hereinabove, it is not intended to limit the invention to such embodiments, but various modifications may be made therein and thereto without departing from the spirit and scope of the invention as set forth in the following claims.

What is claimed is:

1. In a process for preparing fatty acid esters of hydroxyalkyl sulfonic acid salts, said esters having the formula $RCOOR'SO_3M$, where:
   R represents the aliphatic hydrocarbon residue of a fatty acid containing from 6 to 24 carbon atoms,
   R' represents a divalent hydrocarbon radical containing from 2 to 4 carbon atoms, and
   M represents an alkali metal cation, by condensing said fatty acid or a mixture of said fatty acids with a hydroxyalkyl sulfonate of the formula $HOR'SO_3M$, the steps comprising:
   (a) heating a molecular excess of the said fatty acid with said hydroxylalkyl sulfonate, to a temperature of 200° to 250° C., in a substantially oxygen-free atmosphere for sufficient time to remove the water of condensation,
   (b) quenching the hot crude reaction mixture resulting from step (a) by immersing said reaction mixture in a liquid which is at a temperature lower than said reaction mixture and in which said ester is substantially insoluble, but unreacted fatty acids are soluble, thereby to form a slurry wherein the solid phase comprises relatively pure ester of the above formula and the liquid phase comprises said quenching liquid and unreacted fatty acid, and
   (c) separating the solid phase from the liquid phase of said slurry.

2. The process of claim 1, wherein said quench liquid is an organic liquid.

3. The process of claim 1, wherein said quenching liquid is isopropanol.

4. The process of claim 1, wherein said quenching liquid is a component of a detergent formulation.

5. The process of claim 1, in which there is used in step (a) between about 1.1 moles and about 2 moles of said fatty acid per mole of hydroxyalkyl sulfonate.

6. The process of claim 1, in which the separation of step (c) is accomplished by filtration.

7. The process of claim 6, comprising the additional step of distilling the filtrate from step (c) to separate and recover the quenching liquid and unreacted fatty acids.

8. The process of claim 1, in which the hot crude reaction mixture is introduced into from 2 to 5 times its volume of quenching liquid.

9. The process of claim 1, in which the fatty acids are derived from coconut oil.

10. The process of claim 8, wherein the fatty acids comprise a partially hydrogenated coconut fatty acid mixture having an acid value between 266 and 274 mg. KOH/g., an iodine value of 5 max. cg./g., unsaponifiables of 0.5% max., color of less than Gardner 1 and an average molecular weight of 208.

11. The process of claim 1, wherein the hydroxyalkyl sulfonate used in step (a) is introduced in the form of a 40–80% by weight aqueous solution.

12. The process of claim 1, wherein the hydroxyalkyl sulfonate is sodium isethionate.

13. The process of claim 1, wherein the heating step (a) is continued until the crude reaction product contains between 15 and 17% free fatty acid.

14. A process for preparing a fatty acid ester of sodium isethionate which comprises heating together a mixture of fatty acids derived from coconut oil with sodium isethionate, the molar ratio of said fatty acids to said sodium isethionate being from about 1.1 to about 2, while sparging with an inert gas, to a temperature of 200° to 250° C. for a sufficient time to remove the water of condensation and until the crude reaction product contains between 15 and 17% free fatty acid, quenching the hot crude reaction mixture by immersion in from 2 to 5 times its volume of an agitated and cooled liquid in which said ester is insoluble and unreacted fatty acids are soluble, thereby to form a slurry wherein the solid phase comprises relatively pure ester and the liquid phase comprises said quenching liquid and unreacted fatty acid, and filtering said slurry to separate the purified ester from the liquid phase.

15. The process of claim 14, wherein the quenching liquid is isopropanol.

16. A process for purifying a crude fatty acid, hydroxyalkyl sulfonate ester containing unreacted fatty acid which comprises introducing the crude ester in molten form at a temperature of about 200° to about 250° C. into from 2 to 5 times its volume of cooled and agitated quenching liquid and filtering the resulting mixture to separate the purified ester from the filtrate containing quenching liquid and unreacted fatty acids.

17. The process of claim 16, wherein the quenching liquid is isopropanol.

* * * * *